United States Patent [19]
Wellershaus et al.

[11] Patent Number: 4,783,293
[45] Date of Patent: Nov. 8, 1988

[54] PROCESS FOR MANUFACTURING AN INNER CONICAL RECESS FOR RECEIVING AN AMPUTATED EXTREMITY

[75] Inventors: Ulf Wellershaus; Otto Fruzinsky, both of Duderstadt, Fed. Rep. of Germany

[73] Assignee: Otto Bock Orthopaedische Industrie Besitz-und Verwaltungs-Kommanditgesellschaft, Duderstadt, Fed. Rep. of Germany

[21] Appl. No.: 867,955

[22] Filed: May 29, 1986

[30] Foreign Application Priority Data

May 29, 1985 [EP] European Pat. Off. ........ 85106563.1

[51] Int. Cl.⁴ .............................................. B29C 61/02
[52] U.S. Cl. .................................. 264/40.6; 264/40.1; 264/222; 264/230; 264/535
[58] Field of Search ....... 264/535, 230, 222, DIG. 71, 264/DIG. 30, 40.6, 40.1; 623/33-37; 29/447; 156/85

[56] References Cited

U.S. PATENT DOCUMENTS 1,907,511 5/1933 Davies .................. 264/DIG. 71
3,520,002 7/1970 Wellington ..................... 264/222
3,791,098 2/1974 Webster ............................ 264/524
3,823,208 7/1974 Asbelle et al. ..................... 264/222

Primary Examiner—Jan H. Silbaugh
Assistant Examiner—Neil M. McCarthy
Attorney, Agent, or Firm—Foley & Lardner, Schwartz, Jeffery, Schwaab, Mack, Blumenthal & Evans

[57] ABSTRACT

An inner conical recess fitting (1) which is connectable to the prosthesis and is intended for receiving a stump (17) of an amputated extremity can be fitted directly to the stump (17) without the aid of modeling in the following procedural steps: to mold the inner conical recess, a plastic which is shrinkable through the action of external influences, such as heat, is selected; a tube (14) which is made of this plastic and is open at at least one end and has a smaller diameter and a smaller length than the inner conical recess fitting (1) to be manufactured is extended and stretched, so that it has in every direction a greater dimension than the inner conical recess fitting (1) to be manufactured; and the widened and stretched molded piece (10) is placed on the stump (17) and is made to shrink through, e.g., application of heat at selected locations, until the fitting bears everywhere securely against the stump.

4 Claims, 4 Drawing Sheets

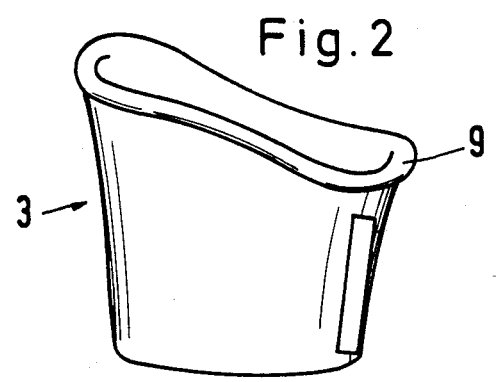
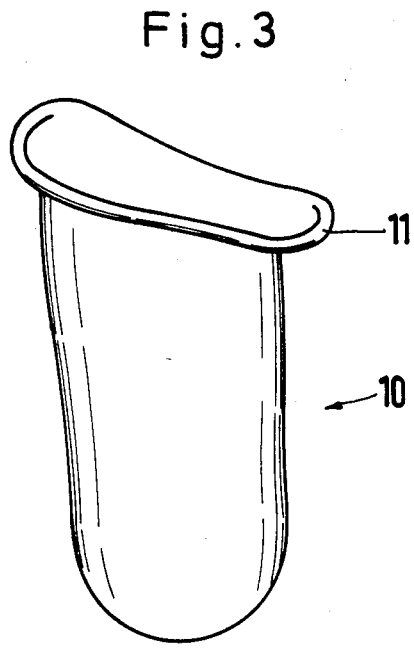

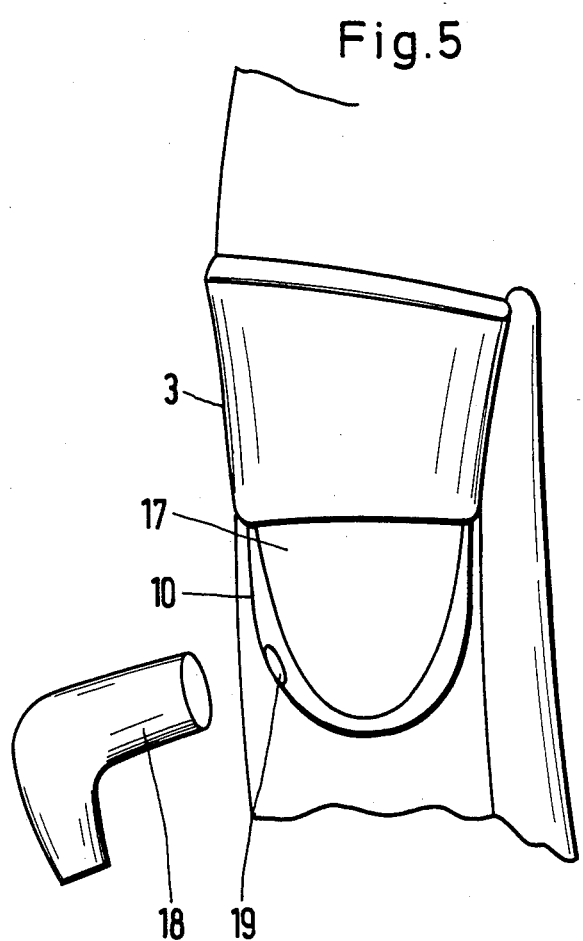

PROCESS FOR MANUFACTURING AN INNER CONICAL RECESS FOR RECEIVING AN AMPUTATED EXTREMITY

BACKGROUND OF THE INVENTION

The present invention relates to a process for manufacturing an inner conical recess or socket which is connectable to a prosthesis and is intended for receiving a stump (pedicle) of an amputated extremity. The invention also relates to a molded piece which is designed for use in a process of the invention.

Inner conical recesses of this type, which directly receive the stumps of amputated extremities and therefore need to have been fitted extremely well to the shape of the specific stump, are manufactured in a completely uniform manner, irrespective of the material used in a specific case. A negative impression is prepared of the stump, for example, from plaster. This impression is filled with a suitable plastic to form the positive impression of the stump. The material of the inner conical recess is applied onto this positive impression, for example, by pouring on a suitable foam material or deep-drawing a thermoplastic sheet. This procedure is self-evidently very time-consuming and expensive. With recent amputees there is an addition the problem that the stump is still undergoing changes which necessitate manufacture of a new shaft with a new inner conical recess a certain time after the amputation. Again the equipping of these patients (interim equipping) is relatively time-consuming. The repeated modeling steps make it impossible to manufacture the inner conical recess having the optimal degree of accuracy.

SUMMARY OF THE INVENTION

It is therefore an object of the present invention to provide an improved process for manufacturing inner conical recesses suitable for receiving an amputated extremity.

A particular object of the invention resides in providing such a process which enables accurate manufacture of the inner conical recess in a less time-consuming way.

It is also an object of the invention to provide a molded part which is suitable for use in the process of the invention, as well as a kit including such a molded part and improved prostheses which are manufactured according to the invention.

In accomplishing the foregoing objects, there has been provided according to one aspect of the invention a process for manufacturing an inner conical recess fitting which is attachable to a prosthesis for receiving a stump of an amputated extremity, comprising the steps of providing a generally conically-shaped hollow molded part comprised of a polymer material which is selectively shrinkable in response to application of an external effect, this molded part being open at its base and being larger in size than the inner conical recess fitting to be produced; placing the molded part directly on the stump of an amputated extremity; and applying to selected local portions of the molded part an external effect suitable to produce shrinkage of the plastic material, this effect being applied in an amount sufficient to produce a degree of shrinkage so that the molded part conforms with the shape of the stump to produce the inner conical recess fitting.

In accordance with another aspect of the invention, there has been provided a molded part suitable for manufacturing an inner conical recess fitting which is attachable to a prosthesis for receiving a stump of an amputated extremity, comprisng a generally conically-shaped hollow molded part comprised of a polymer material which is selectively shrinkable in response to application of an external effect. The molded part is open at its base and has at its base an outwardly curled lip portion. The molded part has generally the shape of the stump which it is intended to receive and has a dimension in each direction, except around the inner circumference of the lip portion, which is larger than the stump which it is intended to receive.

There is also provided according to this invention a kit for manufacturing a prosthesis portion adapted to receive a stump of an amputated extremity, comprising a hollow, generally cylindrical seat ring which is open at both ends and is adapted to be fit around the stump of an amputated extremity, the seat ring having at one end an outwardly curled lip portion; and a molded part as defined above, wherein the molded part is adapted to be inserted into the seat ring prior to fitting of the seat ring around the stump of an amputated extremity and wherein the lip portion of the molded part is adapted to interengage and be supported by the lip portion of the seat ring.

In addition, the invention has provided a prosthesis, comprising at least one prosthesis member and, attached to the prosthesis member, an inner conical recess fitting for receiving the stump of an amputated extremity, wherein the inner conical recess fitting is made according to the process as defined above.

Further objects, features and advantages of the invention will become apparent from the detailed description of preferred embodiments which follows, when considered together with the attached figures of drawing.

BRIEF DESCRIPTION OF THE DRAWINGS

In the drawings:

FIG. 2 shows a seat ring as an individual component;

FIG. 3 shows a molding according to the invention as an individual component;

FIG. 5 schematically illustrates the fitting of the molded piece to the stump which is held in the seat ring, according to the invention.

DETAILED DESCRIPTION OF PREFERRED EMBODIMENTS

Figure 1:
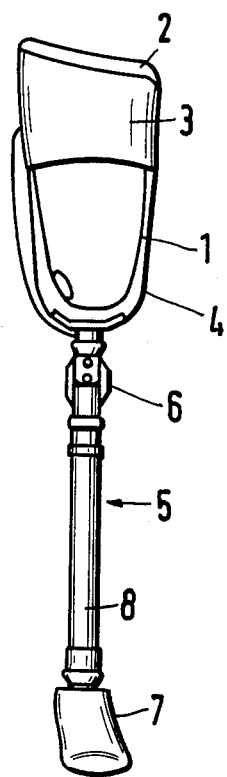
FIG. 1 shows an interim prosthesis having an inner conical recess manufactured in accordance with the invention.

The process of the invention is characterized by the following procedural steps:

to mold the inner conical recess, a plastic which is shrinkable through the action of external influences is selected;

a tube which is made of this plastic and is open at at least one end and has a smaller diameter and a smaller length than the inner conical recess to be manufactured is widened and stretched, so that it has in every direction a greater dimension than the inner conical recess to be manufactured;

the widened and stretched molding is placed on the stump and is made to shrink through local action of the suitable influences until the inner conical recess everywhere bears against and conforms to the stump in the desired manner.

According to the invention, the inner conical recess is thus directly prepared on the stump of the amputated extremity. As a result, it is possible to dispense with the hitherto customary repeated modeling, which led to inaccuracies and required an appreciable amount of time. Fitting to the stump is effected by shrinking the previously expanded plastic part. With the customary shrinkable plastics, this shrinking can be caused through local heat action, which is producible, for example, by hot air from a hair-dryer. This shrinkage is effected at temperatures which are comfortably acceptable to the human body. By means of the localized heating, it is possible to obtain a very accurate fit of the inner conical recess on the stump, indeed through cooperation of the patient, in that the latter can indicate at any time when the desired fit on the stump is obtained in the heated area.

To expand and stretch the plastic tube, it is particularly suitable to use a blow molding process in which the plastic is heated and expanded onto the contour of a blow mold by injection of compressed air.

The inner conical recess can thus be fitted to the stump in a simple manner by using a premanufactured, correspondingly expanded molded piece which is made of a shrinkable plastic. Beginning with a tube which is open at at least one end and has a smaller diameter than the inner conical recess to be manufactured (a "preform"), the molded piece is expanded to a shape which has in every direction a greater internal dimension than the inner conical recess to be manufactured. With such a molded piece, final prostheses as well as interim prostheses can be prepared in a simple manner in orthopedic workshops by means of a hair-dryer.

In a particularly convenient manner it is possible to adapt the inner conical recess to the circumstances of the stump during wear of the prosthesis if the molding has at its open upper edge a curled rim with which it is securable in a premanufactured seat ring adapted to its shape. This arrangement is particularly suitable for producing an interim prosthesis. The seat ring is selected from a plurality of sizes for the size of stump in question. The expanded molded piece is adapted to the seat ring, so that the molded piece can be pushed onto the stump together with the seat ring. The seat ring can readily include a transitional attachment for the prosthesis, for example, one having a knee joint.

The invention will now be explained in more detail by reference to the illustrative embodiments depicted in the drawings.

FIG. 1 shows a leg prosthesis for a patient who has been amputated at the thigh. To receive the thigh stump there is provided an inner conical recess 1 which, by means of an edge 2 at the upper open rim has been suspended in a seat ring 3 of a type which is known. The seat ring 3 is connected with a frame-like support 4 to a known modular prosthesis 5 which has a knee joint and an artificial foot 7, between which a prosthesis tube 8 extends.

FIG. 2 shows a view, from obliquely behind, of a seat ring 3 which has a somewhat oval shape and is adapted to hold in a ring-like manner a thigh stump. The upper rim 9 has been widened outwardly and constructed to be soft. To form the inner conical recess 1, a molded piece 10 (FIG. 3) which is open at the top is suspended from above in the seat ring 3. To this end, the molded piece 10 has at the upper open edge a rim 11 which is bent outwardly and matches the rim 9 of the seat ring 3.

Figure 4:
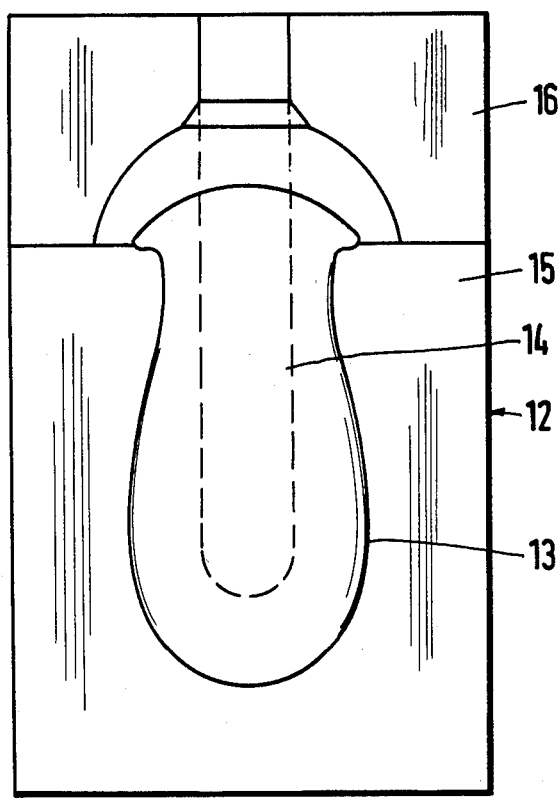
FIG. 4 schematically shows a blow mold for preparing a molding according to the invention.

FIG. 4 illustrates the production of the molded piece 10 in a blow mold 12. The blow mold 12 has a mold contour 13 whose dimensions in every direction are greater than the dimensions of the ultimately required inner conical recess 1. A preform or blank 14, which is drawn in broken lines in FIG. 4, is suspended in the blow mold. The blank has the shape of an oversized test tube. In the blow mold the plastic material of the blank 14 is heated up, and the interior is subjected to compressed air. As a result the blank takes on the contour 13 of the blow mold, so that the molded piece 10 of FIG. 3 results. It is removable after separating the two mold halves 15, 16.

FIG. 5 illustrates that the molded piece 10 is suspended in the seat ring 3 and that this arrangement is pushed over a stump 17 of the amputated extremity. The expanded molded piece 10 has at every location larger dimensions than the stump 17 or the inner conical recess 1 to be produced, so that the stump is in contact with the molded piece 10 only in the upper part of the seat ring 3. Since the size of the seat ring 3 has been selected for the stump 17 in question and the molded piece 10 has been matched to the shape of the seat ring 3, a ring-like fit of the molded piece 10 on the stump 17 is present in the upper region. The remaining fit is then effected through the action of hot air from a hair-dryer 18 on the molded piece 10, as a result of which the latter shrinks in the area of the local heating. By this process the molded piece 10 can be gradually fitted to the shape of the stump 17, the result being the inner conical recess 1 which precisely fits the stump 17.

FIG. 5 additionally shows a circular opening 19 in the molded piece, which serves for passing through the lower end of a tricot stocking which is drawn over the stump 17, so that the plastic of the molded piece 10 does not stick to the skin of the stump 17.

From previous experience it has been found that only a relatively small number of different size seat rings 3 is required to accommodate the various possible sizes of stumps 17. Accordingly only a corresponding number of premanufactured molded pieces 10 is required in order to be able to manufacture the requisite inner conical recess 1 for all stumps 17. Once the inner conical recess 1 has been produced, there is no difficulty in producing a complete prosthesis shaft by applying further plastic coats. In this way it is also possible to provide suitable fastening means for the remaining prosthesis elements.

What is claimed is:

1. A process for manufacturing an inner conical recess fitting which is attachable to a prosthesis for receiving a stump of an amputated extremity of an amputee, comprising the steps of:

providing a generally conically-shaped hollow molded part comprised of a polymer material which is selectively shrinkable in response to application of an external effect, said molded part being open at its base and being larger in size than the inner conical recess fitting to be produced;

placing the molded part directly on the stump of an amputated extremity;

applying to selected local portions of the molded part an external effect suitable to produce shrinkage of the plastic material, said effect being applied in an amount sufficient to produce a degree of shrinkage so that the molded part conforms with the shape of the stump to produce the inner conical recess fitting;

and obtaining a desired fit of the fitting on the stump through indication by the amputee when a desired fit is obtained.

2. A process as claimed in claim 1, wherein said external effect comprises heat.

3. A process as claimed in claim 2, wherein said applying step comprises blowing heated air upon the molded part.

4. A process as claimed in claim 1, wherein said molded part has been formed by heating a hollow preform of the polymer material and expanding the preform under pressure to the shape of the molded part.

* * * * *